United States Patent [19]

Maruyama et al.

[11] Patent Number: 5,017,381

[45] Date of Patent: May 21, 1991

[54] MULTI-UNIT PULSATILE DELIVERY SYSTEM

[75] Inventors: Frederick Maruyama, San Jose; Richard Cortese, Los Gatos, both of Calif.

[73] Assignee: Alza Corporation, Palo Alto, Calif.

[21] Appl. No.: 517,912

[22] Filed: May 2, 1990

[51] Int. Cl.$^5$ ............................................. A61K 9/24
[52] U.S. Cl. ................................... 424/472; 424/438; 424/43; 604/892.1
[58] Field of Search ................. 424/472, 438, 43; 604/892.1

[56] References Cited

U.S. PATENT DOCUMENTS

| | | | |
|---|---|---|---|
| 3,845,770 | 11/1974 | Theeuwes et al. | 128/260 |
| 3,987,790 | 10/1976 | Eckenhoff et al. | 128/260 |
| 3,995,631 | 12/1976 | Higuchi et al. | 128/260 |
| 4,034,756 | 7/1977 | Higuchi et al. | 128/260 |
| 4,111,202 | 9/1978 | Theeuwes | 128/260 |
| 4,320,759 | 3/1982 | Theeuwes | 128/260 |
| 4,449,983 | 5/1984 | Cortese et al. | 604/892 |
| 4,578,263 | 3/1986 | Whitehead | 424/15 |
| 4,642,230 | 2/1987 | Whitehead et al. | 424/15 |
| 4,723,958 | 2/1988 | Pope et al. | 604/890 |
| 4,765,837 | 8/1988 | Whitehead | 75/249 |
| 4,874,388 | 10/1989 | Wong et al. | 604/891 |

FOREIGN PATENT DOCUMENTS

WO86/00519 1/1986 PCT Int'l Appl. .
2206047A 12/1988 United Kingdom .

Primary Examiner—Merrell C. Cashion, Jr.
Assistant Examiner—D. Gabrielle Phelan
Attorney, Agent, or Firm—Jacqueline S. Larson; Edward L. Mandell; Steven F. Stone

[57] ABSTRACT

The present invention is directed to an active agent dispenser for use in a fluid-containing environment, which dispenser comprises a rigid housing, a plurality of movable active agent units filling a portion of the housing, a fluid-activated driving member for dispensing the active agent units filling the remainder of the housing, and an active agent unit outlet means. In the present invention, each active agent unit is comprised of an active agent dosage or filling contained within a fluid-impermeable cup-shaped member, the cup-shaped members being oriented within the housing with the base of the cup-shaped members facing the outlet means.

23 Claims, 2 Drawing Sheets

MULTI-UNIT PULSATILE DELIVERY SYSTEM

FIELD OF THE INVENTION

This invention relates to patterned drug delivery. More particularly, this invention relates to patterned drug delivery by means of a plurality of individual drug delivery units. Still more particularly, but without limitation thereto, this invention relates to delivery of multi-agents orally or in other media in a preprogrammed delivery profile.

RELATED PATENT APPLICATIONS

This application is related to the copending, coassigned U.S. Pat. applications Ser. No. 07/495,825, filed on Mar. 19, 1990, of Wong et al. for Multi-Unit Delivery System; Ser. No. 07/283,772, filed on Dec. 13, 1988, of Wong et al. for Multi-Unit Delivery System; Ser. No. 07/283,631, filed on Dec. 13, 1988, of Wong et al for Multi-Layer Delivery System; and Ser. No. 07/270,160, filed on Nov. 14, 1988, of Wong et al. for Multi-Layer Delivery System.

BACKGROUND OF THE INVENTION

The concept of patterned drug delivery covers a broad range of systems from time-release capsules whose components have coatings which erode at different rates, to controlled release rate tablets which operate by osmosis.

Despite the development in the art, however, there remains a continuing need for improved methods and systems for providing controlled drug release profiles, and particularly pulsed release profiles.

SUMMARY OF THE INVENTION

An object of this invention is to provide sequential timing and dispensing of dosage units containing the same or different active agents.

Another object of this invention is to provide sequential timing and dispensing of two dosage units simultaneously, the units containing the same or different active agents.

A third object of this invention is to provide a delivery system with a rate of delivery that is independent of the chemical or physical properties of the active agent used.

A further object of this invention is to provide a means for protecting the active agent within the dosage units from degradation by a fluid-containing environment until each dosage unit is released into the environment.

Yet another object of this invention is to provide both a novel and a useful agent formulation pulsatile delivery system that is self-contained and self-powered, and also represents an improvement in the delivery art.

These and other objects are demonstrated by the present invention wherein an active agent dispenser for use in a fluidcontaining environment comprises a rigid housing, a plurality of movable active agent units filling a portion of the housing, a fluidactivated driving member for dispensing the active agent units filling the remainder of the housing, and an active agent unit outlet means. In the present invention, each active agent unit is comprised of an active agent dose or filling contained within a fluidimpermeable cup-shaped member, the cup-shaped members being oriented within the housing with the base of the cup-shaped members facing the outlet means.

DETAILED DESCRIPTION OF THE INVENTION

Figure 1:
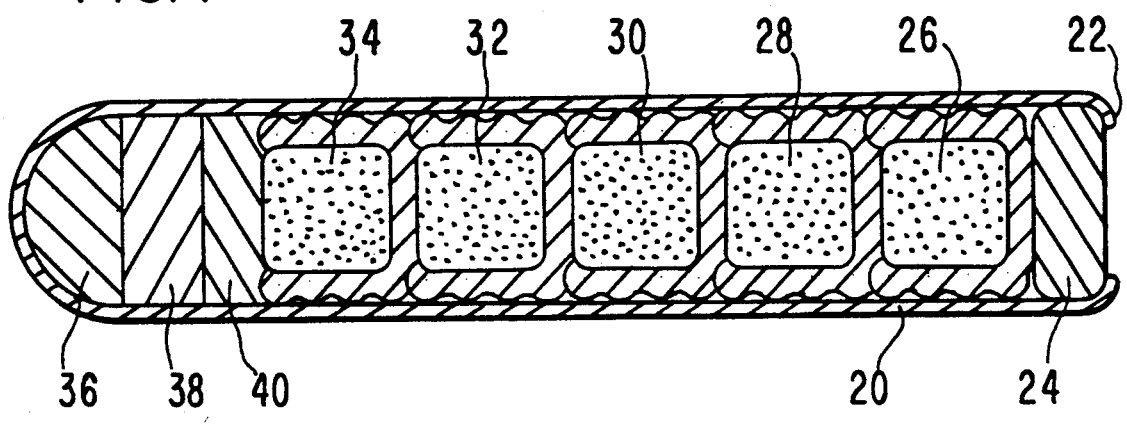
FIG. 1 is a cross-sectional view illustrating one embodiment of the dispenser of this invention.

In the following discussion, like reference numerals refer to like elements in the figures.

This invention can provide a variety of drug or active agent delivery profiles including, but not limited to, pulsed delivery of a single drug or drug formulation, pulsed delivery of a sequence of different drugs or drug formulations, and pulsed delivery of two drugs or drug formulations simultaneously.

The terms "active agent" and "drug" are used interchangeably herein, and as used herein broadly include any compound, composition of matter, or mixture thereof that can be delivered from the system to produce a beneficial and useful result. This includes pesticides, herbicides, germicides, biocides, algicides, rodenticides, fungicides, insecticides, anthelmintics, parasiticides, antioxidants, plant growth promoters, plant growth inhibitors, preservatives, antipreservatives, disinfectants, sterilization agents, catalysts, chemical reactants, fermentation agents, foods, food supplements, nutrients, cosmetics, drugs, vitamins, minerals, sex sterilants, fertility inhibitors, fertility promoters, air purifiers, microorganism attenuators and other agents that benefit the The terms "active agent" and "drug" as used herein further include any physiologically or pharmacologically active substance that produces a localized or systemic effect or effects in animals' including warm-blooded mammals, humans and primates; avians; domestic household, sport or farm animals such as dogs, sheep, goats, cattle, horses and pigs; laboratory animals such as mice, rats and guinea pigs; fish; reptiles; zoo animals; or wild animals. The active agent or drug which can be delivered includes inorganic and organic compounds, including, without limitation, those materials that act upon the central nervous system such as hypnotics, sedatives, psychic energizers, tranquilizers and anticonvulsants; muscle relaxants; muscle contractants; antiparkinson agents; analgesics; anti-inflammatories; local anesthetics; antimicrobials; antimalarials; hormonal agents including contraceptives; sympathomimetrics; diuretics; lipid regulating agents; antiandrogenic agents; neoplastics; antineoplastics; hypoglycemics; nutritional agents; fats; ophthalmic agents; electrolytes; and diagnostic agents.

The terms "drug unit", "dosage unit", "active agent unit" and "active agent dosage unit" as used herein include units that are capable of maintaining their physical configuration and chemical integrity while housed within the dispenser. The terms "drug tablet" and "active agent tablet" include, without limitation, tablets with or without a density element; matrix tablets; pellets and elongated tablets where the height-to-diameter ratio exceeds one; capsules; elementary osmotic pumps, such as that described in U.S. Pat. No. 3,845,770; mini-osmotic pumps, such as those described in U.S. Pat. Nos. 3,995,631, 4,034,756 and 4,111,202; and multichamber osmotic systems referred to as push-pull and push-melt osmotic pumps, such as those described in U.S. Pat. Nos. 4,320,759 and 4,449,983; all of which are incorporated herein by reference.

As used herein, the expression "fluid" includes water and biological fluids.

The drug delivery system or dispenser of this invention is designed to deliver a plurality of discrete longitudinally aligned individual drug units by the linear expansion of a fluid-activated driving member. The drug units are such that they retain their physical and chemical integrity while contained within the system and do not commence delivery of active agent until after they have been dispensed into the environment. This is accomplished by having the drug units comprise a drug dosage contained within an impermeable cup- or cap-shaped member. The dispenser is comprised of a dispensing component and a driving component, representative embodiments of which are disclosed in U.S. Pat. No. 4,874,388, the entire disclosure of which is incorporated herein by reference. The dispensing and driving component designs are for use in a fluidcontaining environment and are merely exemplary of the numerous embodiments suitable for use in this invention.

The portion of the housing adjacent to the dispensing component is of a material which may be either semipermeable or substantially impermeable to the passage of external fluid. The material of the housing is additionally chemically compatible with the active agent contained in the drug units positioned therein, and, in the instance of providing a drug or like depot within the body of a living organism, is biologically inert, non-irritating to body tissues and non-allergenic. In a preferred embodiment, the material is also flexible and insoluble. Typical suitable semipermeable and impermeable materials are discussed in U.S. Pat. No. 4,874,388 (supra).

At least a portion of the housing adjacent to the driving component must be semipermeable so as to allow for passage of external fluid, since the driving member is fluid-activated. Again, where the device is to be used within the body of a living organism, the housing material is biologically inert, non-irritating to tissues and non-allergenic. Suitable materials are discussed at length in U.S. Pat. No. 4,874,388 (supra).

While the dispenser housing is most commonly insoluble under the conditions and in the environment of intended use, it is also within the scope of the invention that such materials be insoluble only during the period of the intended use, thereafter dissolving or otherwise degrading into the environment of the device. Thus, a dispenser is here contemplated which is unaffected by its environment, solubility-wise, at the situs of use, or which is only slightly soluble during the period of intended use, but once all the units have been dispensed, it will then dissolve or erode away, leaving no objectionable residue or empty container at the situs of use.

The dispenser shown in FIG. 1 is comprised of a rigid semipermeable housing member 20. Housing 20 is designed with an outlet means, exit port 22. The housing contains a driving member 38 opposite exit port 22. A plurality of movable discrete drug units 26, 28, 30, 32 and 34 are aligned within the housing 20 between the driving member 38 and the exit port 22. This configuration is merely illustrative, and the dispenser may have drug units of a number other than the number shown in FIG. 1.

Figure 2:
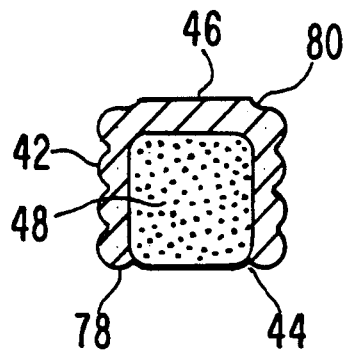
FIG. 2 is a cross-sectional view illustrating one embodiment of an active agent unit of this invention.

As shown in FIG. 2, the drug units are in the form of a fluidimpermeable cup-shaped member 42 with an open end 44 and a closed end or base 46, the cup 42 containing within it a dose or filling 48 of an active agent which may be in tablet, powdered, paste or other practical form. A drug tablet is preferred. The cup may be in any of a variety of forms having a base and sides and an open end and being capable of holding a drug dosage or filling, such as a tablet.

The material of the cup 42 is selected from those which are impermeable to the fluid environment and to the drug and other components of the dose or filling 48, and is inert to the components of the filling. Typical suitable impermeable materials include, without limitation, polyethylene, compressed polyethylene fine powder, polyethylene terephthalate (Mylar ®), plasticized polyvinyl chloride, metal-foil polyethylene laminates, neoprene rubber, natural gum rubber, rubber hydrochloride (Pliofilm ®), thermoplastic elastomers, polystyrene, polypropylene, polyvinyl chloride, reinforced epoxy resin, polymethylmethacrylate, sheet metal (e.g., aluminum, copper, steel, etc.), or styrene/acrylonitrile copolymer. In a presently preferred embodiment, the cup 42 is made of a thermoplastic elastomer. Examples of thermoplastic elastomers include, without limitation, polyester/polyether copolymer, polypropylene/ethylene-propylene-diene monomer (EPDM) copolymer, polypropylene/crosslinked EPDM copolymer (Santoprene ®, Monsanto), and polyethylene/crosslinked EPDM copolymer. In one embodiment, the material making up the cup 42 is insoluble only during the period of intended use, thereafter dissolving or otherwise degrading into the fluid environment. This is particularly desirable when the dispenser is to be placed in the body of an animal.

The base 46 of the cup-shaped member 42 is aligned in the housing facing the exit port 22, as illustrated in FIG. 1. Thus, the cup acts to protect the drug dosage or filling 48 from action by the fluid environment until the entire drug unit, 26 for example, is released into the environment.

The dispenser of FIG. 1 may also optionally include an initial drug or active agent tablet 24 that is not contained within a cup-shaped member. This initial tablet 24 is included when it is desired to provide an initial dose of a drug immediately or very shortly after the dispenser has been placed into the fluid environment.

The dispenser of FIG. 1 includes a driving member 38 that is fluid-activated. Many different types of fluid-activated driving components are known in the art, examples of which are discussed in detail in U.S. Pat. No. 4,874,388, incorporated previously herein by reference, and may include a water-swellable composition, an osmotically effective solute, an elementary osmotic pump or a gasgenerating composition, for example. An inert layer 40 may optionally be present to separate the driving member 38 from the drug units, 34 for example. Layer 40, in a presently preferred embodiment, comprises a composition that is substantially impermeable to the passage of fluid, and it serves to restrict the passage of fluid present in the expandable driving member 38 into the compartment housing the drug units. Thus, layer 40 should have suitable properties to form a water-tight but movable seal between itself and the inner surface of the container. Alternately, where the driving member 38 includes a gas-generating composition, layer 40 may comprise a semipermeable membrane that is impermeable to the gasgenerating composition but is permeable to the gas generated by the composition. Layer 40 further operates to essentially maintain the integrity of the drug units and the driving component 38. Layer 40 acts also to insure that the expanding driving force generated by the driving component is applied directly against the drug units.

In operation of the device of FIG. 1, as driving member 38 imbibes fluid through the semipermeable housing 20 adjacent thereto, it expands linearly to displace inert layer 40, if present, and the drug units, 24 and 26 for example, towards the exit port 22. As initial drug tablet 24 comes into contact with the exit, it is dispensed into the environment and begins to deliver drug in a controlled or semicontrolled fashion. Once initial tablet 24 is dispensed, linear displacement pushes drug unit 26 through the housing 20 so that it then comes into contact with exit port 22 and is likewise dispensed. This continues until the dispenser is depleted of drug units.

As the drug units, 26 for example, are pushed toward and through the exit port 22, first the base 46 and then the sides of the impermeable cup 42 are exposed to the fluid environment. However, because the cup is impermeable, the drug dosage or filling 48 remains unexposed and protected from the environment until such time as the unit has completely passed through exit port 22 and is released from the dispenser. Only when the drug unit has fallen away from the housing so that open end 44 of the cup is exposed to the environment does the drug dosage come into contact with the environment, at which time the drug to be delivered is dispensed.

Upon exposure, the drug dosage or filling 48 can erode, disintegrate, burst as a result of osmotic action or otherwise release the drug into the environment. The release may be immediate upon exposure or it may be slower, as by controlled erosion for example. The doses can be designed in a multitude of ways to provide a specific drug delivery profile. Besides protecting the drug dosage or filling from premature exposure to the environment, the configuration of this invention guarantees that the drug being delivered to the environment comes from the dispensed unit rather than from the units still retained within the housing.

Figure 7:
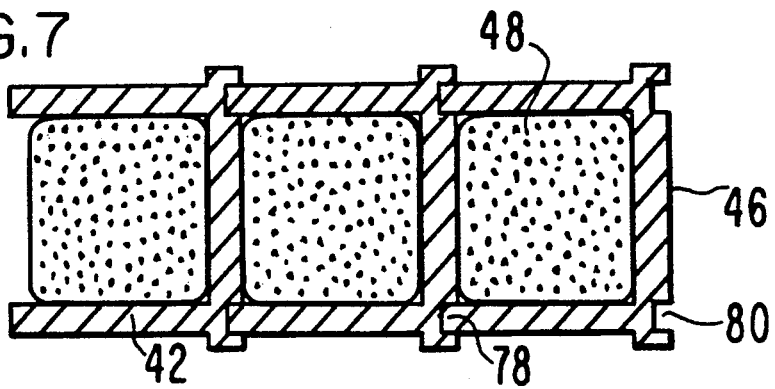
FIG. 7 is a sectional view of three of the active agent units in another embodiment of the invention.

A pulsed delivery of active agent to the environment is provided by cup member 42, which produces a delay or "off" period, during which time no drug is being delivered. To achieve such a result prior to the present invention, it was necessary to alternate drug units or layers with non-drug-containing units or layers or with inert partitions within the dispenser. These non-drug-containing layers took up valuable space and often made the dispenser unacceptably large or bulky for the intended use. By using the cup-shaped member, non-drug layers are not required. Also, with the cup member, the length of time between pulses of delivered drug can be accurately regulated by the physical characteristics of the cup. More particularly, the intervals between pulses may be determined by the length of the sides of the cup-shaped member or, in other words, by the depth of the cup-shaped member. Thus, shorter "off" periods and more frequent pulses are provided when the cup is relatively shallow, so that the period of time required for a drug unit to move through the exit port along the entire length of its sides and be expelled into the environment is short. Longer "off" periods between pulses of drug are obtained with relatively deeper cups. The interval between pulses of drug may be varied within a single dispenser by placing drug units of different depths into the housing, as illustrated in FIG. 7. A variety of drug delivery rate profiles are therefore possible and can be tailored to the particular use and/or drug regimen desired. Use of the drug units of the present invention provides an advantage over previous devices in that the delivery rate can be independent of the chemical or physical properties of the drug to be delivered.

The drug units of the present invention can also provide a variety of drug delivery profiles depending upon the composition of the drug dosage or filling within the units. The drug fillings can all contain the same drug(s) at the same concentration(s) to deliver identical pulses of drug over time as each unit is dispensed, or they can contain the same drug(s) at different concentrations to give different pulses of drug. Alternately, the fillings may contain different drugs or drug formulations. In addition, the duration of the pulse itself can be varied by adjusting the dispersion characteristics of the drug filling to provide for a longer or shorter duration of the pulse. Further, the various drug units or the various fillings within the units need not be uniform in size. Also, if it is desired to have a longer interval between pulses of drug than that provided by the physical dimensions of cup 42 alone, the cup may contain a filling 48 that comprises a biologically inactive material rather than an active agent. Such biologically inactive materials may be selected from suitable biodegradable materials such as waxes, soluble glasses, biodegradable polymers, compressed powders, plaster of Paris, hydrophobic gels such as petrolatum, and the like. Or, the cup may contain no filling at all.

Thus, it is apparent that the duration of the drug delivery pulses and the intervals between drug delivery pulses may be readily varied to provide for a pulsatile drug delivery device with rate characteristics to match any situation desired by selecting the appropriate physical dimensions of the cup-shaped member of the drug units; dissolution or dispersion characteristics, concentration, or physical dimensions of the drug filling; and rate characteristics of the driving member.

In a preferred embodiment of the invention, the drug dosage or filling is a drug tablet. The tablet may be a solid core or a matrix tablet or in any of a variety of forms which are capable of maintaining their physical and chemical integrity while within the housing environment. The drug tablets of this invention may contain, in addition to the active agent, inert ingredients such as binders, lubricants, dyes, diluents, fillers, surfactants, excipients such as compounds to stabilize the active agent or to facilitate erosion or disintegration, and other components known in the art. An example of a suitable composition as contemplated by this invention is about 80-95 wt% drug, about 2-3 wt% binder, about 0.1-5 wt% lubricant, about 1-15 wt% excipient to facilitate disintegration or erosion and about 1-6 wt% excipient to stabilize the drug. The drug tablet composition may also be modified to include about 0.1-5 wt% of a surfactant Materials suited for use in formulating the drug tablets of this invention are well known in the art and are fully described in texts such as *Pharmaceutical Sciences*. Remington, 17th Ed. (1985), Mack Publishing Co., Easton, Pa. Examples are also disclosed in U.S. Pat. No. 4,874,388 (supra).

The dispenser of the present invention is especially suitable for use as a bolus in ruminants such as cattle and sheep. For ruminal systems, an important criterion is that the system remain in the rumen of an animal over a prolonged period of time. This may be provided either by the dispenser having a suitable geometric configuration, for example by being equipped with wings as described in PCT Application WO 86/00519 or, more preferably, by placement of a density element within the dispenser. The housing itself or a portion of the housing may be the density element. Alternately, a density element such as density element 36 in FIG. 1 may be placed so as to remain within the housing after all of the drug-containing units have been dispensed.

The density element suitable for use in the dispenser of this invention must be dense enough to retain the dispenser in the rumenreticular sac of a ruminant. The presence of a density element allows the dispenser to remain in the rumen over a prolonged period of time rather than letting it pass into the alimentary tract and be eliminated therefrom. As the dispenser remains in the rumen, a beneficial agent can be delivered to the ruminant at a controlled rate over an extended period of time. Generally, a density element will have a density of from about 0.8 to 8 g/ml, or higher, with the density in a presently preferred embodiment exhibiting a specific gravity of from about 2.2 to 7.6 g/ml, and more preferably from about 2.5 to 3.5 g/ml.

The density element may be made from any suitable material or combination of materials sufficient to achieve the overall required bolus density. For example, the density element may be fabricated from a generally inert material such as iron, steel, stainless steel, copper, copper oxide, iron shot coated with iron oxide, a mixture of cobalt oxide and iron powder, chromium, nickel, and the like, or an alloy of metals. Alternately, a generally degradable material may be used, such as, for example, a degradable zinc or magnesium alloy. The density element may, if desired, comprise a matrix of materials, for example shot of iron or other metal dispersed in an inert (e.g. polymer) or degradable (e.g. magnesium alloy) base material.

Figure 3:
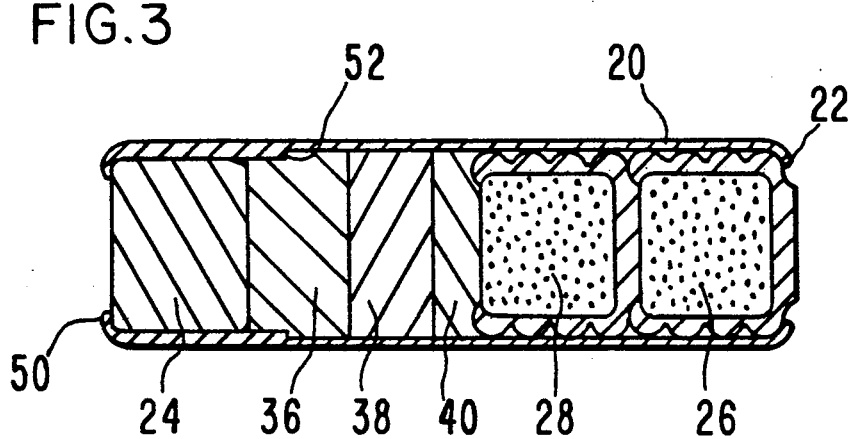
FIG. 3 is a cross-sectional view illustrating a second embodiment of the dispenser of this invention.

The dispenser of FIG. 3 illustrates another embodiment of the invention, which comprises a rigid semipermeable housing 20 with a first exit port 22 at one end and with a second exit port 50 at the end of the housing 20 opposite first exit port 22. A driving member 38 is present within the housing between the two exit ports. There are a plurality of discrete drug units 26 and 28 aligned within the housing between the driving member 38 and first exit port 22, the units being oriented with the base of the cup-shaped members facing the first exit port. Two drug units are shown, but in actual application any number of units may be used. An inert layer 40 may optionally be present to separate the driving member 38 from the drug units, 28 for example. Initial drug tablet 24, which is not contained in a cup-shaped member, is adjacent second exit port 50, and density element 36 is between initial drug tablet 24 and driving member 38. When the dispenser is placed in a fluid environment, initial drug tablet 24, which is exposed to the fluid through exit port 50, immediately begins to erode upon contact with the fluid, releasing drug into the environment. This provides an initial burst or dose o drug. The wall of housing 20 is thicker in the region surrounding initial drug tablet 24 and a portion of density element 36, creating a ridge 52 into which the density element fits or rests, so that once initial drug tablet 24 has eroded away, the ridge will act to retain the density element in the housing. At the same time, driving member 38 becomes activated to displace drug units 26 and 28 toward and out the first exit port 22.

Figure 4:
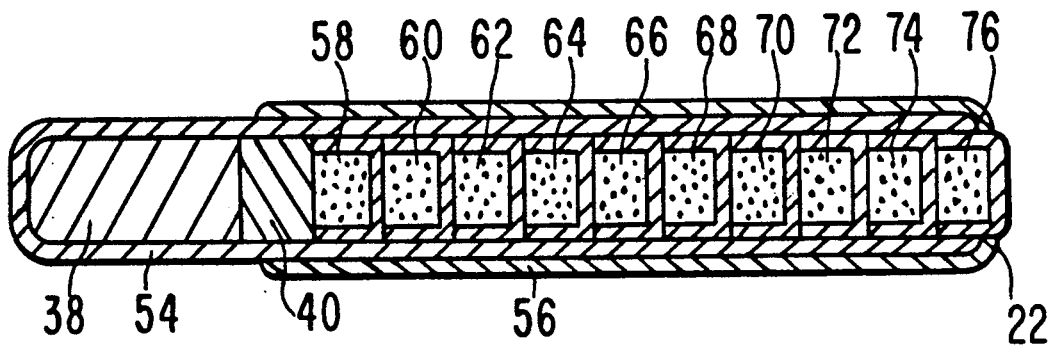
FIG. 4 is a cross-sectional view illustrating still another embodiment of the dispenser of this invention.

The dispenser shown in FIG. 4 has a housing comprised of a semipermeable membrane 54 and an impermeable membrane 56, the impermeable membrane enclosing the dispensing component portion of the dispenser. A plurality of discrete drug units 58-76 are aligned within the portion of the housing enclosed by impermeable membrane 54, the units being oriented with the base of the cup-shaped members facing the exit port 22. As with FIGS. 1 and 3, the number of units shown is merely illustrative and is not intended to limit the invention in any manner. The driving member 38 operates to linearly displace inert layer 40 and the drug units to dispense the units through the exit port 22. In this embodiment, no initial drug tablet is present, so that there is no immediate initial release of active agent.

Figure 5:
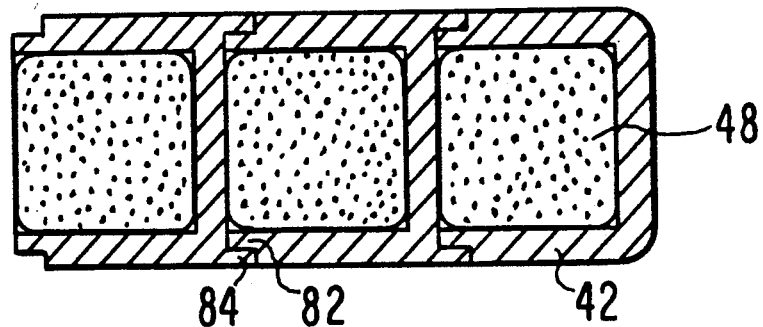
FIG. 5 is a sectional view of three of the active agent units in one embodiment of the invention, stackably engaged.
Figure 6:
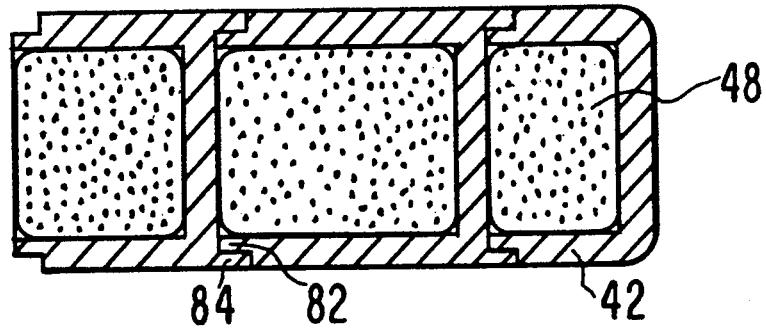
FIG. 6 is a sectional view of three of the active agent units in another embodiment of the invention, stackably engaged.

In a preferred embodiment of the invention, the individual drug units are stackably engageable one with another so that the units are properly aligned within the housing. Two different embodiments that provide one method of doing this are illustrated in FIGS. 2 and 6. In these embodiments, the end of the wall of cup-shaped member 42 defines a ridge 78 that locates in a corresponding groove 80 in base 46 of cup 42, thus inhibiting relative movement. In another method, illustrated in FIG. 5, the units are held together by an annular protrusion 82 on each cup 42 being an interference fit into a complementary socket 84 in the next adjacent cup.

Drugs that are suitable for delivery by the dispenser systems of this invention are of a wide range and variety and can include those that have limited solubility or are very slightly soluble or insoluble in water or biological fluids as well as those that are soluble or very soluble in such fluids. Examples of such drugs are listed in U.S. Pat. No. 4,874,388, previously incorporated herein by reference. The drug can also be in the various chemical and physical forms such as uncharged molecules, molecular complexes, and pharmacologically acceptable acid addition and base addition salts such as hydrochlorides, hydrobromides, sulfates, laurylates, oleates and salicylates. For acidic drugs, salts of metals, amines or organic cations, for example quaternary ammonium, can be used. Derivatives of drugs such as esters, ethers and amides can be used along or mixed with other drugs. Also, a drug that is waterinsoluble can be used in a form that, on its release from the dispenser, is converted by enzymes, hydrolyzed by body pH or other metabolic processes to the original form, or to a biologically active form.

The amount of drug incorporated in the drug units of the dispenser of this invention varies widely depending on the particular drug, the desired therapeutic effect, and the time span necessary for the drug to be released. Since a variety of units in a variety of sizes, shapes and compositions are intended to provide complete dosage regimes for therapy for a variety of maladies, there is no critical upper limit on the amount of drug incorporated in the units of the invention. The lower limit, too, will depend on the activity of the drug and the time span of its release from the units. Thus, it is not practical to define a range for the therapeutically effective amount of drug to be released by the individual units or by the dispenser as a whole.

While the present invention has been described and illustrated with reference to certain preferred embodiments thereof, it should not be construed as being limited thereto. Various modifications, changes, omissions, and substitutions that are obvious to those of skill in the art can be effected within the spirit and scope of the invention and are intended to be within the scope of the following claims.

What is claimed is:

1. An active agent dispenser for use in a fluid-containing environment comprising, in combination:
   a. a rigid housing open at one end to provide outlet means therefor, at least a portion of said housing proximate the end of said housing opposite said outlet means permitting passage of the fluid in said environment to the interior of said housing;
   b. a fluid-activated driving member within said housing in fluid-transmitting relationship with said fluid-passing portion of said housing proximate the end of said housing opposite said outlet means, said driving member, upon exposure of said dispenser to said fluid environment, being the source of motive power for moving the contents of said housing through said outlet; and
   c. a plurality of discrete active agent dosage units, each unit comprising:
      (i) a fluid-impermeable cup-shaped member, and
      (ii) an active agent filling contained within said cup-shaped member, wherein said active agent dosage units are longitudinally disposed within said housing between said driving member and said outlet means and are oriented within said housing with the base of said cup-shaped members facing said outlet means; whereby said active agent dosage units will be sequentially displaced from said housing into said fluid environment by said driving member upon exposure of said dispenser to said fluid environment, said active agent dosage units dispensing their active agent content into said fluid environment after their displacement from said housing into said environment.

2. The dispenser of claim 1 wherein said plurality of active agent dosage units contain the same active agent.

3. The dispenser of claim 1 wherein said plurality of active agent dosage units contain different active agents.

4. The dispenser of claim 1 wherein said active agent filling is an active agent tablet.

5. The dispenser of claim 1 wherein said driving member comprises a fluid-swellable composition.

6. The dispenser of claim 1 wherein said driving member comprises an osmotically effective solute.

7. The dispenser of claim 1 wherein said driving member comprises an elementary osmotic pump.

8. The dispenser of claim 1 wherein said driving member comprises a gas-generating composition.

9. The dispenser of claim 1 which further comprises an inert layer between said driving member and said active agent dosage units.

10. The dispenser of claim 1 which further comprises a density element.

11. The dispenser of claim 1 which further comprises an comprises an initial active agent tablet which is not contained in a fluid-impermeable cup-shaped member.

12. The dispenser of claim 1 wherein said active agent dosage units are stackably engaged one with another.

13. An active agent dispenser for use in the rumen of a ruminant, the dispenser comprising, in combination:
   a. a rigid housing open at one end to provide outlet means therefor, at least a portion of said housing proximate the end of said housing opposite said outlet means permitting passage of the fluid in said environment to the interior of said housing;
   b. a fluid-activated driving member within said housing in fluid-transmitting relationship with said fluid-passing portion of said housing proximate the end of said housing opposite said outlet means, said driving member, upon exposure of said dispenser to said fluid environment, being the source of motive power for moving the contents of said housing through said outlet;
   c. a density element within said housing; and
   d. a plurality of discrete active agent dosage units, each unit comprising:
      (i) a fluid-impermeable cup-shaped member, and
      (ii) an active agent filling contained within said cup-shaped member, wherein said active agent dosage units are longitudinally disposed within said housing between said driving member and said outlet means and are oriented within said housing with the base of said cup-shaped members facing said outlet means; whereby said active agent dosage units will be sequentially displaced from said housing into said fluid environment by said driving member upon exposure of said dispenser to said fluid environment, said active agent dosage units dispensing their active agent content into said fluid environment after their displacement from said housing into said environment.

14. The dispenser of claim 13 which further comprises an inert layer between said driving member and said active agent dosage units.

15. The dispenser of claim 13 which further comprises an initial active agent tablet which is not contained in a fluid-impermeable cup-shaped member.

16. The dispenser of claim 13 wherein said plurality of active agent dosage units contain the same active agent.

17. The dispenser of claim 13 wherein said plurality of active agent dosage units contain different active agents.

18. The dispenser of claim 13 wherein said active agent filling is an active agent tablet.

19. The dispenser of claim 13 wherein said active agent dosage units are stackably engaged one with another.

20. The dispenser of claim 1 wherein the portion of said housing adjacent said active agent dosage units is impermeable to the fluid in said fluid environment.

21. The dispenser of claim 1 wherein the portion of said housing adjacent said active agent dosage units is permeable to the fluid is said fluid environment.

22. The dispenser of claim 13 wherein the portion of said housing adjacent said active agent dosage units is impermeable to the fluid in said fluid environment.

23. The dispenser of claim 13 wherein the portion of said housing adjacent said active agent dosage units is permeable to the fluid in said fluid environment.

* * * * *